United States Patent
Takeda

Patent Number: 5,293,404
Date of Patent: Mar. 8, 1994

[54] THERMAL MEASURING AND TESTING SYSTEM HAVING SYNCHRONIZED SAMPLE TRANSPORTING MEANS

[75] Inventor: Haruo Takeda, Tokyo, Japan
[73] Assignee: Seiko Instruments Inc., Tokyo, Japan
[21] Appl. No.: 799,060
[22] Filed: Nov. 27, 1991

[30] Foreign Application Priority Data
Nov. 29, 1990 [JP] Japan .................. 2-339874

[51] Int. Cl.$^5$ .................. H05B 1/02; G01N 25/00
[52] U.S. Cl. .................. 373/136; 373/135; 219/521; 432/43; 432/45; 432/121; 374/12; 374/11
[58] Field of Search .................. 373/136, 135, 115, 113; 219/390, 405, 411, 521, 385; 392/416, 418; 118/724, 725, 50.1, 728; 432/45, 121, 43; 374/12, 11, 15

[56] References Cited
U.S. PATENT DOCUMENTS

| | | | |
|---|---|---|---|
| 1,227,027 | 1/1917 | Baily et al. | 432/43 |
| 3,982,882 | 9/1976 | Weingrad | 432/43 |
| 4,609,343 | 9/1986 | Tejfalussy | 432/36 |
| 4,690,569 | 9/1987 | Veitch | 374/12 |

Primary Examiner—Bruce A. Reynolds
Assistant Examiner—John A. Jeffery
Attorney, Agent, or Firm—Spensley Horn Jubas & Lubitz

[57] ABSTRACT

A thermal analysis device with a sample transporting machine which automatically carries out pretreatment of a sample to quickly heat or cool it. The configuration includes an electric furnace, a temperature controller, a temperature program setter, a sample placing/removing program setter, and a sample transporter, wherein the said sample placing/removing program setter commands the said sample transporter to place the said sample in or remove it from the said electric furnace in synchronization with a synchronization signal from the said temperature program setter and in accordance with a preset sample placing/removing program and, hence, the said sample placing and removing operations (i.e. to place a sample in the electric furnace or, conversely to remove a sample from the electric furnace) are carried out in the electric furnace which is performing a heating operation or a cooling operation in accordance with a temperature program output by the said temperature program setter.

4 Claims, 1 Drawing Sheet

THERMAL MEASURING AND TESTING SYSTEM HAVING SYNCHRONIZED SAMPLE TRANSPORTING MEANS

The present invention relates to a thermal measuring and testing system adapted to provide temperature data for analysis on a sample to be tested.

A control device of a conventional thermal analysis device of this type has not been equipped with a sample placing/removing program setter and has controlled only placing and removing operations in synchronization with the start and termination of the operation of a temperature program generator. Therefore, a sample has been placed in an electric furnace at the start of the operation of the said temperature program generator and has not been removed from the electric furnace until the operation is terminated and, as a result, there has been no way to quickly heat or cool a sample other than quickly heating or cooling the electric furnace itself.

In the conventional method of quickly heating or cooling an electric furnace itself to quickly heat or cool a sample, the number of times the temperature of an electric furnace is changed has been limited to only a few times per second because the thermal capacity of an electric furnace is very large in general. Therefore, it has had a problem that it does not allow thermal analysis and measurement including pretreatment such as quench cooling wherein the temperature of a sample must be changed several tens or hundreds of times per second.

SUMMARY OF THE INVENTION

The present invention has been conceived to solve the above problem and mainly comprises an electric furnace, a temperature controller, a temperature program setter, a sample placing/removing program setter and a sample transporter.

According to the present invention having the above configuration, the temperature program setter first starts its operation to output temperature signals in accordance with a preset temperature program to the temperature controller in a sequence of steps from the first step to the final step. It concurrently outputs a synchronization signal to the sample placing/removing program setter at each step. The temperature controller controls the temperature of the electric furnace in accordance with the said temperature signals. On the other hand, upon input of each synchronization signal, the sample placing/removing program setter outputs a transportation command to the sample transporter on the basis of a present sample placing/removing program comprising steps from the first step to the final step. Upon receipt of a transportation command, the sample transporter performs a placing operation or a removing operation which is to hold a sample and place it in the electric furnace or, conversely, to remove it from the electric furnace.

Therefore, it is possible to perform the quick heating pretreatment of a sample by putting the electric furnace in a high-temperature state at the first step of the temperature program and by placing the sample in the electric furnace with the sample transporter at the second step of the sample placing/removing program. Conversely, it is possible to perform quick cooling pretreatment by removing a sample from the electric furnace with the sample transporter after raising the temperature of the electric furnace with the sample placed therein.

BRIEF DESCRIPTION OF DRAWING

The FIGURE is an illustration of a thermal measuring and testing system which is an embodiment of the present invention.

DETAILED DESCRIPTION

Figure 1:
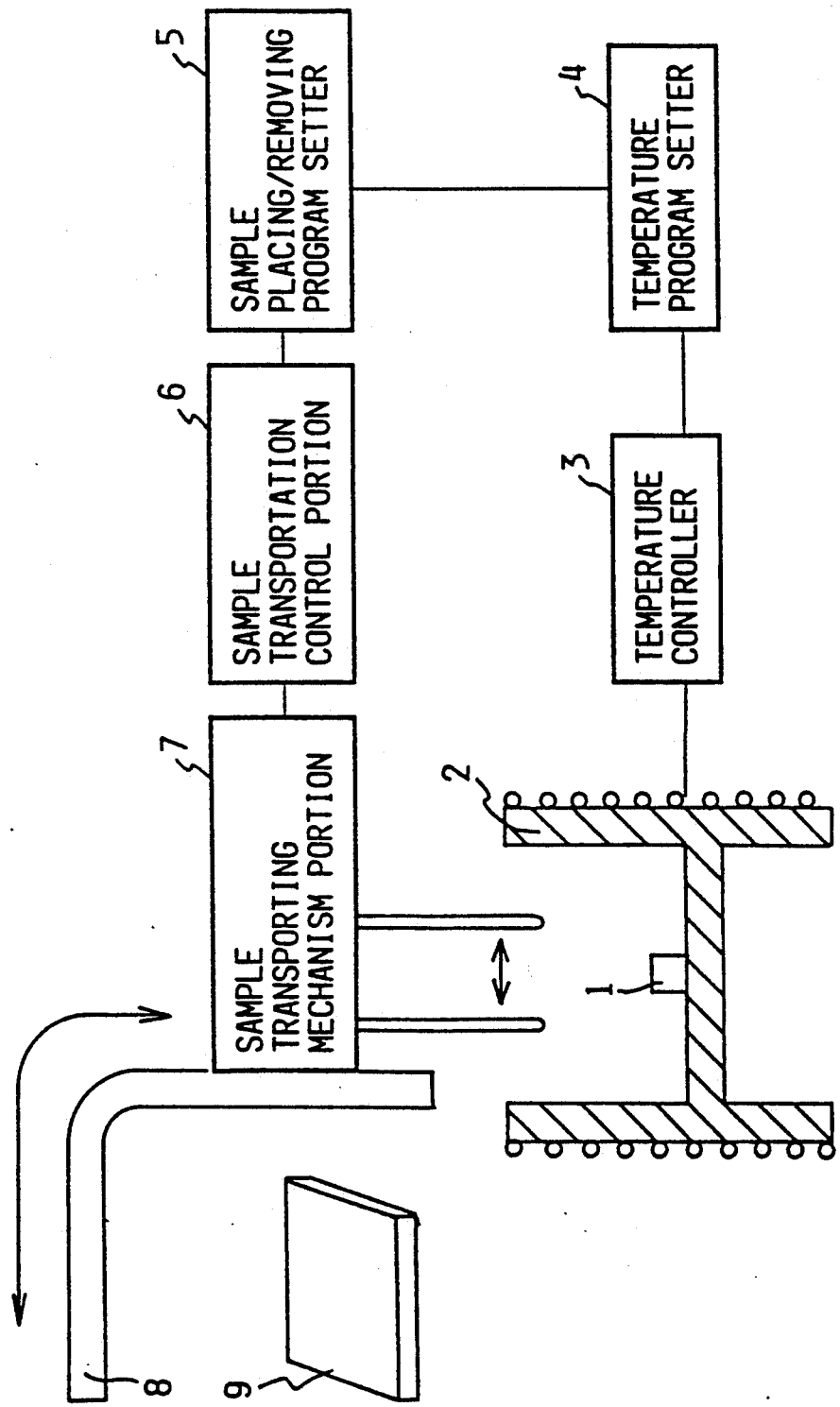

An embodiment of the present invention will now be described in detail with reference to the drawings wherein numeral 1 represents a sample which is placed in an electric furnace 2 and the electric furnace 2 is connected to a temperature controller. A temperature program setter 4 is connected to the temperature controller 2 and a sample placing/removing program setter 5. The sample placing/removing program setter 5 is connected to a sample transportation control portion 6 which is connected to a sample transporting mechanism portion 7. The sample transporting mechanism portion 7 is capable of moving along a transportation movement guide 8 which is mechanically connected thereto, holding a sample 1 placed in the electric furnace 2 and transporting the sample to a sample tray 9 provided in a place which is apart from the electric furnace 2. Conversely, it is capable of holding a sample placed on the sample tray 9 and moving along the transportation movement guide 8 to transport the sample to the electric furnace 2. The sample transportation control portion 6, the sample transporting mechanism portion 7 and the transportation movement guide 8 constitue a sample transporter.

Next, the operation of the sample transporter according to the present invention will now be described. First, a plurality of steps are preset in the temperature program setter 4 to make a desired temperature program, setting for one step of a temperature program comprising values for starting temperature, final temperature, the rate of temperature rise and drop between the starting and final temperature, and a period of time during which the final temperature is to be maintained. On the other hand, sample placing and removing commands are preset in the sample placing/removing program setter 5 for a plurality of steps each corresponding to one of the steps of the temperature program set in the temperature program setter 4. There are three kinds of sample placing and removing commands, i.e., a command to transport the sample 1 from the electric furnace 2 to the sample tray 9 with the sample transporter, a command to transport the sample from the sample tray to the electric furnace 2, and a command to perform no transportation operation at all. The sample 1 is placed on the sample tray 9.

When the device is started in this state, the temperature program setter 4 outputs a temperature signal in accordance with the preset temperature program at a first step to the temperature controller 3 and outputs a synchronization signal to the sample placing/removing program setter 5. The temperature controller 3 has the input of the temperature signal from the temperature program setter 4 which varies every moment, and performs control so as to equalize this temperature and the temperature of the electric furnace 2. However, since the thermal capacity of the electric furnace 2 is large, the temperature of the electric furnace 2 follows the input temperature signal with a delay. Then, after finishing the temperature program at the first step, the temperature program setter 4 sequentially outputs temperature programs at second and third steps to the temperature controller 3 and, each time of this output, it outputs a synchronization signal to the sample placing-/removing program setter 5.

The sample placing/removing program setter 5 to which the synchronization signal has been input for each step, proceeds with the steps of the preset sample placing/removing program one by one to output a sample placing command or a sample removing command corresponding to the temperature program to the sample transporter. The sample transporter which has received the sample placing command or sample removing command performs transportating operations such as holding the sample and placing it in the electric furnace 2 from the sample tray 9, placing it on the sample tray 9 from the electric furnace conversely, and doing nothing.

Therefore, if the temperature of the electric furnace 2 is sufficiently stabilized at the first step of the temperature program and the sample 1 is then placed in the electric furnace 2 by controlling the sample transporter at the second step of the sample placing/removing program, the temperature of the sample 1 whose thermal capacity is very small, will be quickly raised by the conduction of the heat from the electric furnace 2 which is in a high-temperature state. In other words, the quick heating pretreatment of the sample has been simply performed. It is now possible to proceed to measurement.

If, conversely, the electric furnace 2 is kept in the high-temperature state with the sample 1 placed in the electric furnace 2, and the sample 1 is held by the sample transporter to be removed from the electric furnace 2, the temperature of the sample 1 whose thermal capacity is very small, is quickly lowered by the transfer of heat to the holding mechanism portion 7 whose thermal capacity is large and by radiation to the atmosphere. In other words, quick cooling treatment is performed. Thereafter, the electric furnace 2 is controlled so that its temperature becomes the starting temperature for measurement in accordance with the temperature program. Thermal analysis and measurement with cooling pretreatment can be carried out by setting programs in the temperature program setter 4 and the sample placing-/removing program setter 5 such that the sample 1 is placed in the electric furnace with the sample transporter again when the temperature of the electric furnace 2 has become the starting temperature for measurement.

The present invention is not limited to the present embodiment. The temperature controller 3, the temperature program setter 4, and the sample placing/removing program setter 5 may be configurated using either of analog and digital circuits. The holding means of the sample transporter may be configurated using either a type of holding means which mechanically holds or an air chuck type. A configuration in which the functions of the temperature program setter 4 and the sample placing/removing program setter 5 are integrated, may be employed.

As described above, according to the present invention, a sample placing/removing program setter is provided between a sample transporter and a temperature program setter, and a sample placing command or a sample removing command set in the sample placing-/removing program setter, is output to the sample transporter, in accordance with a temperature program set in a temperature program setter, to control an operation to place the sample in or to remove it from the electric furnace. As a result, there is an advantage that measurement including quick heating pretreatment and quick cooling pretreatment can be automatically carried out.

What is claimed is:

1. In a thermal measuring and testing system adapted to provide temperature data for analysis on a sample to be tested, the improvement wherein said thermal measuring and testing system comprises:
    an electric furnace in which a sample is placed;
    a temperature controller which controls the temperature of said electric furnace;
    a temperature program setter which outputs temperature control information to said temperature controller, for setting serial steps which have start temperatures, finishing temperatures, heating or cooling rates and holding periods at finishing temperatures, and outputting synchronization signals at each step;
    a sample placing/removing program setter connected for receiving said synchronization signals of each of said serial steps from said temperature program setter for outputting, in response to each synchronization signal, a selected one of a preset sample maintaining command for maintaining the sample in its existing position, a sample placing command for placing the sample in said electric furnace and a sample removing command for removing the sample from said electric furnace; and
    a sample transporter which holds the sample and places the sample in or removes the sample from said electric furnace according to a sample placing command or a sample removing command from said placing/removing program setter.

2. A thermal measuring and testing system as defined in claim 1 wherein said temperature program setter outputs a given synchronization signal when said electric furnace has been heated to a start temperature, and said sample placing/removing program setter outputs a sample placing command in response to the given synchronization signal.

3. A thermal measuring and testing system as defined in claim 2 wherein said sample placing/removing program setter is programmed to output selected ones of the commands in a selected order and outputs each command in turn in response to a respective synchronization signal.

4. A thermal measuring and test system as defined in claim 1 wherein said sample placing/removing program setter is programmed to output selected ones of the commands in a selected order and outputs each command in turn in response to a respective synchronization signal.

* * * * *